United States Patent
Nichogi et al.

(10) Patent No.: US 11,399,910 B2
(45) Date of Patent: Aug. 2, 2022

(54) MEDICAL SYSTEM

(71) Applicant: OLYMPUS CORPORATION, Tokyo (JP)

(72) Inventors: Masao Nichogi, Kanagawa (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 226 days.

(21) Appl. No.: 16/992,214

(22) Filed: Aug. 13, 2020

(65) Prior Publication Data
US 2020/0367986 A1 Nov. 26, 2020

Related U.S. Application Data

(63) Continuation of application No. PCT/JP2018/005741, filed on Feb. 19, 2018.

(51) Int. Cl.
*A61B 34/00* (2016.01)
*G06F 3/02* (2006.01)

(52) U.S. Cl.
CPC ........ *A61B 34/74* (2016.02); *A61B 2034/742* (2016.02); *G06F 3/02* (2013.01)

(58) Field of Classification Search
CPC ... A61B 2034/742; A61B 34/76; A61B 34/37; A61B 34/35; A61B 34/74; A61B 2034/743; A61B 2090/378; A61B 90/361; A61B 2034/2048; A61B 2034/2059; G06F 3/02
See application file for complete search history.

(56) References Cited

U.S. PATENT DOCUMENTS

2009/0192524 A1 7/2009 Itkowitz et al.
2012/0130399 A1* 5/2012 Moll ............... G16H 30/20
606/130
(Continued)

FOREIGN PATENT DOCUMENTS

EP 3254640 A1 12/2017
EP 3311768 A1 4/2018
(Continued)

OTHER PUBLICATIONS

International Search Report dated Apr. 10, 2018 issued in PCT/JP2018/005741.

*Primary Examiner* — Hang Lin
(74) *Attorney, Agent, or Firm* — Scully, Scott, Murphy & Presser, P.C.

(57) ABSTRACT

A medical system includes: a medical instrument; at least one arm including at least one joint and motor that drive the at least one joint, the at least one arm including an attachment portion for detachably attaching the medical instrument to a distal end; a first input device located remote from the arm and configured to perform an operation input for operating the medical instrument and the at least one arm; a second input device provided at a distal end of the arm and configured to perform an operation input for operating the medical instrument and the at least one arm; and a processor that controls the at least one arm and the medical instrument based on an operation input from the first or second input device. The medical system enables switching in order to selectively accept an operation input from the first or second input device.

11 Claims, 9 Drawing Sheets

(56) References Cited

U.S. PATENT DOCUMENTS

| | | |
|---|---|---|
| 2013/0131867 A1* | 5/2013 | Olds ................ B25J 9/0084 |
| | | 700/260 |
| 2014/0276950 A1 | 9/2014 | Smaby et al. |
| 2015/0073597 A1 | 3/2015 | Olds et al. |
| 2017/0035519 A1 | 2/2017 | Smaby et al. |
| 2017/0325903 A1 | 11/2017 | Nichogi et al. |
| 2017/0340397 A1 | 11/2017 | Smaby et al. |
| 2018/0098817 A1 | 4/2018 | Nichogi |
| 2019/0083185 A1 | 3/2019 | Smaby et al. |

FOREIGN PATENT DOCUMENTS

| | | |
|---|---|---|
| JP | 2009-034813 A | 2/2009 |
| JP | 2012-521855 A | 9/2012 |
| JP | 5467510 B2 | 4/2014 |
| JP | 2015-501729 A | 1/2015 |
| JP | 2016-052521 A | 4/2016 |
| JP | 2016-101506 A | 6/2016 |
| JP | 2016-518878 A | 6/2016 |
| WO | WO 2010/117685 A2 | 10/2010 |
| WO | WO 2013/067535 A1 | 5/2013 |
| WO | WO 2014/146090 A1 | 9/2014 |
| WO | WO 2016/125574 A1 | 8/2016 |
| WO | WO 2016/203858 A1 | 12/2016 |

\* cited by examiner

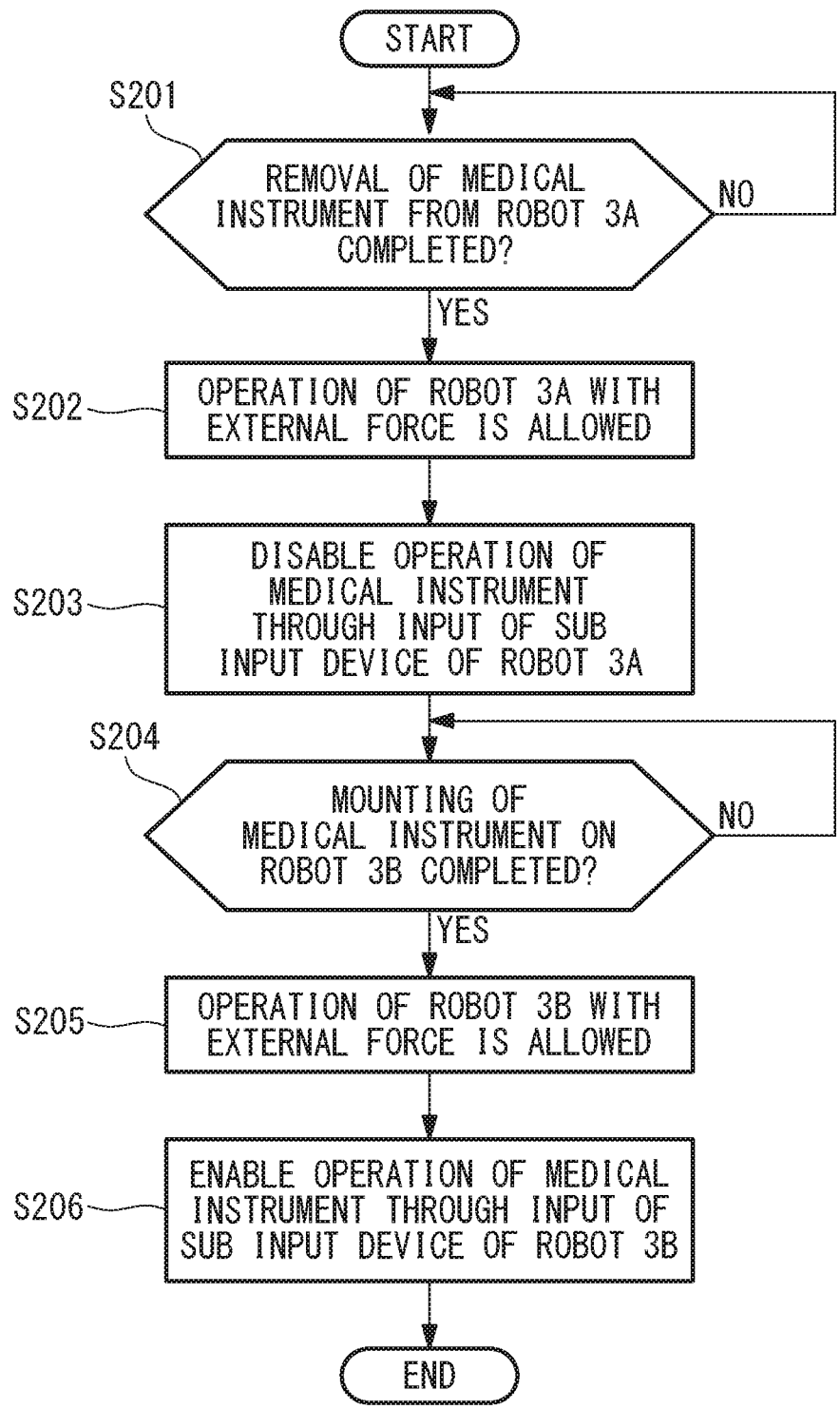

MEDICAL SYSTEM

CROSS-REFERENCE TO RELATED APPLICATIONS

This is a continuation of International Application PCT/JP2018/005741 which is hereby incorporated by reference herein in its entirety.

TECHNICAL FIELD

The present invention relates to a medical system.

BACKGROUND ART

There is a known medical system that includes a manipulator and a medical instrument at a distal end of a robot arm and that controls the robot arm, the manipulator, and the medical instrument to perform an operation on a patient through an operation input portion that is located remote from the patient (for example, see PTL 1).

CITATION LIST

Patent Literature

{PTL 1} Japanese Examined Patent Application, Publication No. WO2016/203858

SUMMARY OF INVENTION

According to an aspect of the present invention, a medical system includes: a medical instrument that has a treatment portion at a distal end thereof; at least one arm that includes at least one joint and at least one motor that drives the at least one joint, the at least one arm including an attachment portion for detachably attaching the medical instrument at a distal end; a first input device that comprises a handle and that is located remote from the at least one arm, the first input device being configured to perform an operation input for operating the medical instrument and the at least one arm, the medical instrument being attached to the attachment portion of the at least one arm; a second input device provided at a distal end of the at least one arm, the second input device being configured to perform an operation input for operating the medical instrument and the at least one arm, the medical instrument being attached to the attachment portion of the at least one arm; and a processor that controls the at least one arm and the medical instrument on the basis of an operation input that is input from the first input device or the second input device. The medical system enables switching in order to selectively accept an operation input from the first input device or the second input device. The second input device includes a grip rotatable about a longitudinal axis of the medical instrument attached to the attachment portion, and a first switch. The processor, on the basis of a signal from the switch, switches between a synchronous mode in which the medical instrument is rotated about the longitudinal axis in synchronization with rotation of the grip, and an asynchronous mode in which the medical instrument is not rotated even when the grip is rotated.

In another aspect of the present invention, a medical system includes: an arm that is configured to attach a medical instrument having a treatment portion at a distal end thereof and that includes at least one joint, the arm including: a sensor provided at the at least one joint, the sensor detecting an external force applied to the arm; a first motor that drives the at least one joint; and a second motor that drives the medical instrument; a first input device that includes a handle and that is located remote from the arm, the first input device being configured to perform an operation input for operating the medical instrument and the arm; a second input device provided at a distal end of the arm, the second input device being configured to perform an operation input for operating the medical instrument and the arm, the second input device including: a grip provided at an end of the arm to directly operate the arm; a button provided at the grip to operate the medical instrument; and a switch that enables switching in order to selectively accept an operation input from the first input device or the second input device; and a processor that controls the first motor and the second motor, wherein the processor: controls the first motor on the basis of an amount of the external force detected by the sensor when the grip is directly operated in a state where the operation input from the second input device is ready to be accepted; detect, after controlling the first input device, whether or not the button is operated; and control, in response to detecting that the button is operated, the second motor on the basis of the operation input of the second input device.

BRIEF DESCRIPTION OF DRAWINGS

FIG. 9 is a flowchart illustrating another modification of the control of the medical system in FIG. 4.

DESCRIPTION OF EMBODIMENTS

A medical system 1 according to an embodiment of the present invention will be described below with reference to the drawings.

Figure 1:
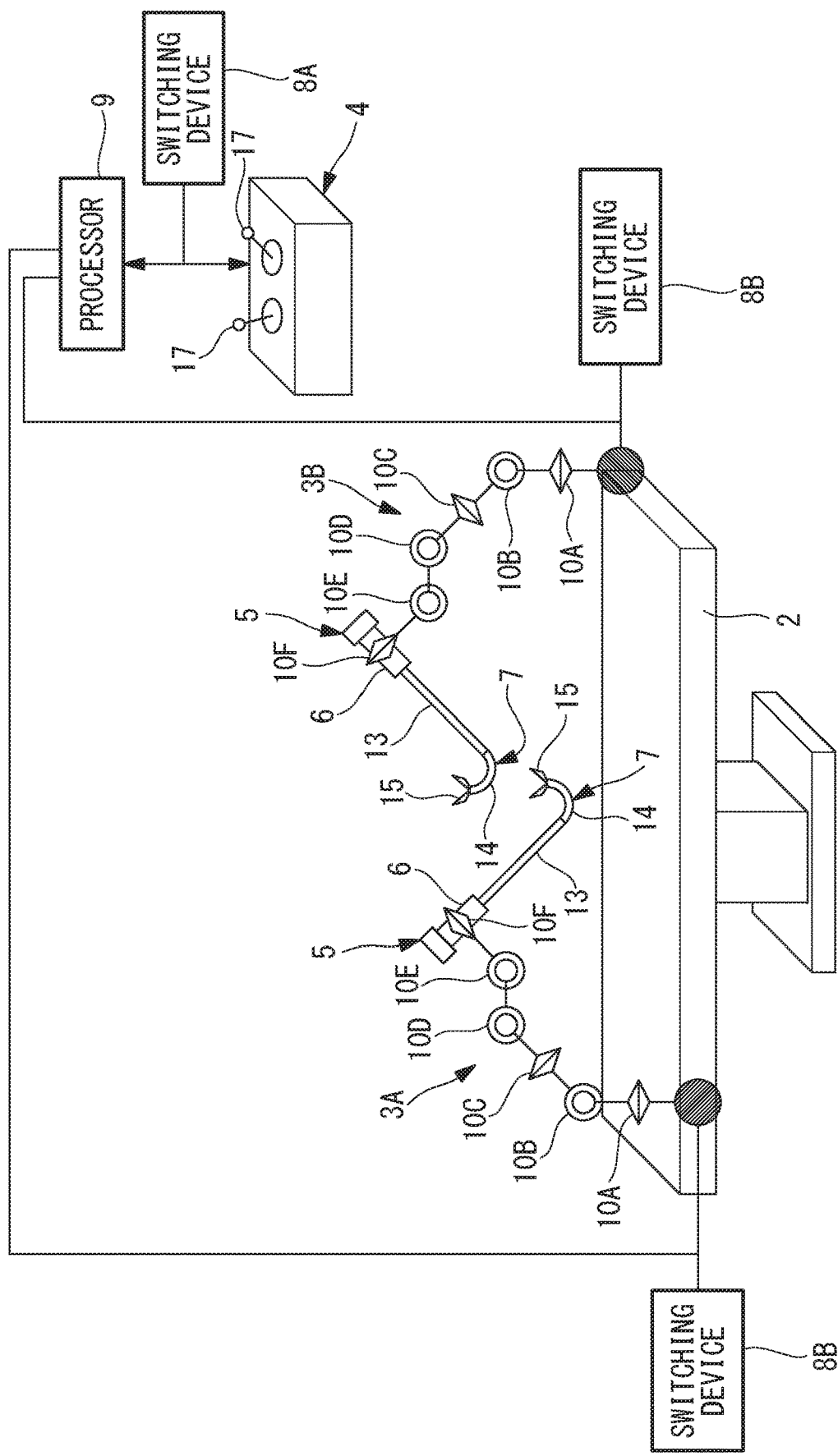
FIG. 1 is an overall configuration diagram illustrating a medical system according to an embodiment of the present invention.
Figure 2:
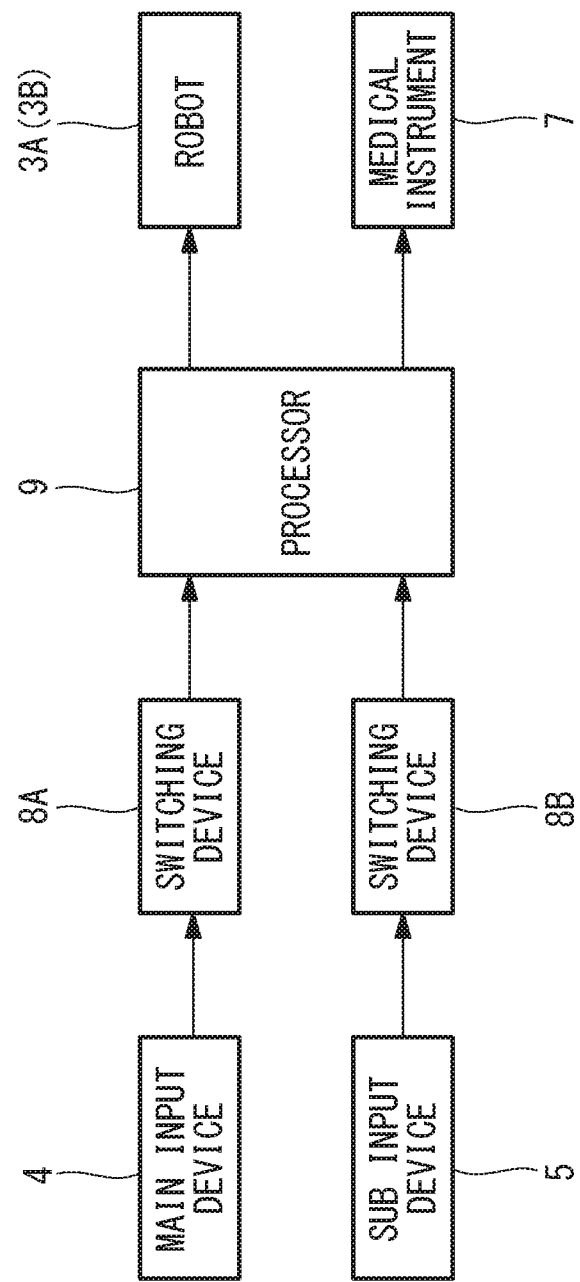
FIG. 2 is a block diagram illustrating the medical system in FIG. 1.

The medical system 1 according to the present embodiment includes, as illustrated in FIGS. 1 and 2, two robots (arms) 3A, 3B installed near a bed 2 on which a patient is lying, a main input device (first input device) 4 disposed at a position remote from the bed 2, sub input devices (second input devices) 5 respectively provided at distal ends of the robots 3A, 3B, medical instruments 7 respectively detachably attached to attachment portions 6 respectively provided at distal ends of the robots 3A, 3B, switching devices 8A, 8B respectively provided in the main input device 4 and the sub input devices 5, and a processor 9 that controls the robots 3A, 3B and the medical instruments 7 on the basis of operation inputs that are input through the main input device 4 and the sub input devices 5.

The two robots 3A, 3B are 5-axis articulated robots, and each of five joints 10A, 10B, 10C, 10D, 10E includes a motor (driving device; not illustrated) driven in accordance with a command signal and a force sensor (sensor; not illustrated) that detects an external force. The motors of the joints 10A, 10B, 10C, 10D, 10E are provided with encoders (not illustrated), and the encoders detect the rotation angles of the joints 10A, 10B, 10C, 10D, 10E. A joint 10F of a sixth axis is provided at the farthest distal end of the robot 3A, 3B. The joint 10F of the sixth axis will be referred to in the description of the sub input devices 5 described later.

The medical instruments 7 each include, for example, an insertion portion 13 that is to be inserted into a body by penetrating body surface tissue, a manipulator portion 14 having one or more joints protruding forward from a distal end of the insertion portion 13, and a treatment portion 15 that is provided at the distal end of the manipulator portion 14 and that is used to perform treatment on tissue in the body.

Figure 3:
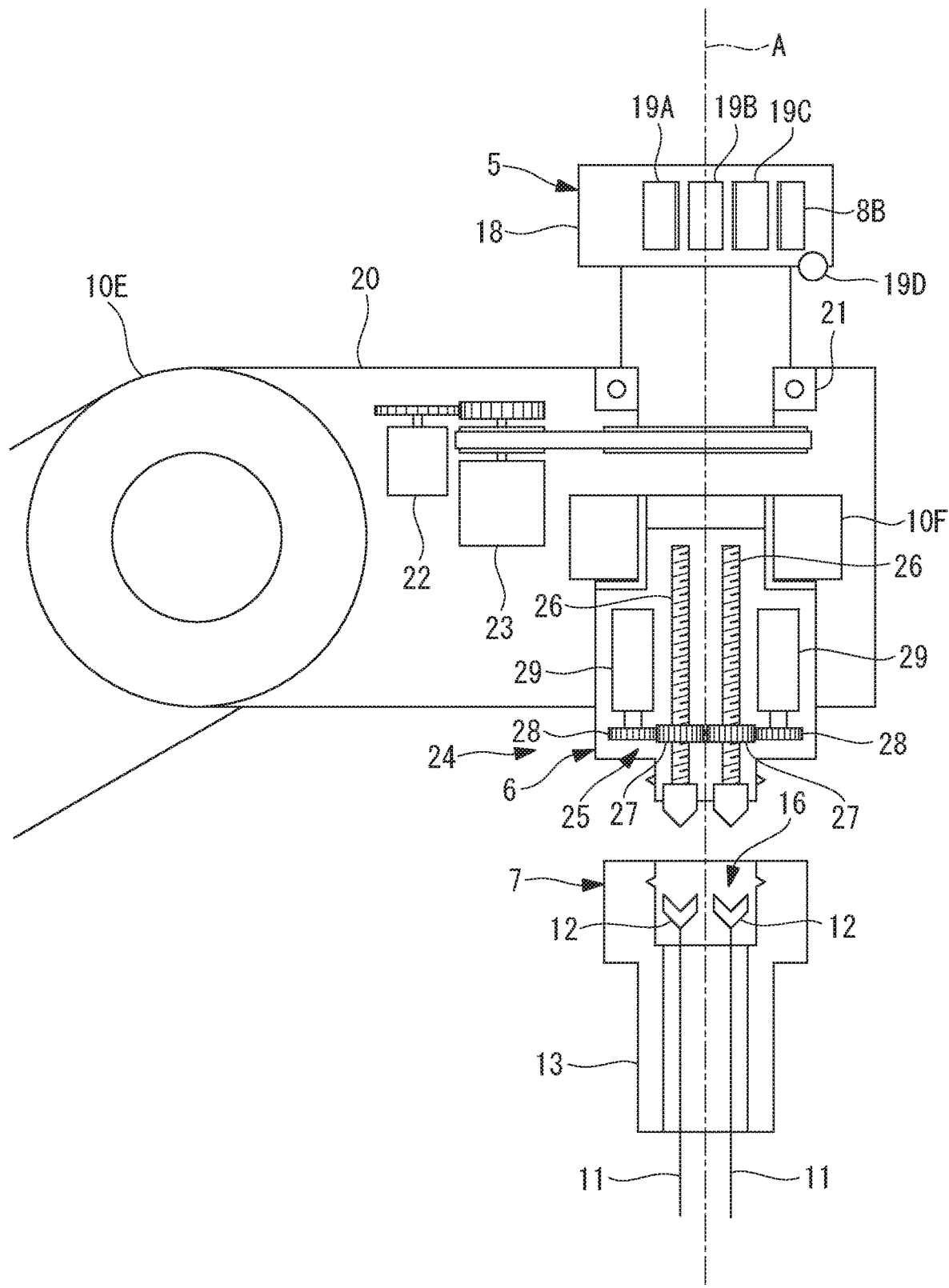
FIG. 3 is a diagram illustrating details of a second input device and a medical instrument provided at a distal end of a robot constituting the medical system in FIG. 1.

As illustrated in FIG. 3, a connector portion 16 is provided at a proximal end of the insertion portion 13 so as to be detachably attached to the attachment portion 6 of the robot 3A, 3B. Proximal ends of motive power transmission members 11, such as wires or rods, which are connected to the manipulator portion 14 and the treatment portion 15 and which are for driving the manipulator portion 14 and the treatment portion 15, are disposed in the connector portion 16.

In addition, the connector portion 16 is provided with attachment-detachment mechanisms 12 for detachably attaching to the detachable portion 6 of the robot 3A, 3B. The attachment-detachment mechanisms 12 become mutually engaged when the connector portion 16 is attached to the attachment portion 6 to hold the medical instrument 7 in an attached state at the distal end of the robot 3A, 3B, and the medical instrument 7 can be easily removed from the distal end of the robot 3A, 3B by operating a release means (not illustrated) to release the engagement.

The main input device 4 includes handles 17 that are held and operated by the right and left hands of the operator. For example, one robot 3A and the medical instrument 7 attached to the robot 3A can be operated by operating the handle 17 held by the right hand, and the other robot 3B and the medical instrument 7 attached to the robot 3B can be operated by operating the handle 17 held by the left hand.

Each of the sub input devices 5 is attached to a distal end of the corresponding robot 3A, 3B and includes, for example, a grip 18 to be held by the surgeon, and a plurality of buttons (switches) 19A, 19B, 19C provided on the grip 18. When an external force is applied to the grip 18 held by the surgeon, the external force transmitted to the robot 3A, 3B is detected by force sensors provided at the joints 10A, 10B, 10C, 10D, 10E. Consequently, the surgeon can input an external force as an operation input.

In addition, by operating any of the buttons 19A, 19B, 19C provided on the grip 18 held by the surgeon, the manipulator portion 14 and the treatment portion 15 of the medical instrument 7 can be operated. Specifically, the button 19A is a first bending button for bending the manipulator portion 14 in one direction, the button 19B is a gripping button for operating the treatment portion 15, and the button 19C is a second bending button for bending the manipulator portion 14 in another direction.

More specifically, as illustrated in FIG. 3, the sub-input device 5 includes the grip 18 that has a columnar shape and that is rotatably attached to a base member 20, which is rotated by the joint 10E of a fifth axis at a distal end of the robot 3A, 3B, around a sixth axis (sixth axis) A of the robot 3A, 3B by a bearing 21, and an encoder 22 that detects a rotation angle of the grip 18. Reference sign 23 denotes a brake that locks the rotation of the grip 18.

The base member 20 is provided with a motor (not illustrated) rotatable about the sixth axis A, and a medical instrument driving portion 24 can be rotated about the sixth axis A by the motor.

The medical instrument driving portion 24 includes the attachment portion 6 for detachably attaching the connector portion 16 through the attachment-detachment mechanisms 12 of the medical instrument 7, and a drive mechanism 25 that connects to an end portion of each of the motive power transmission members 11 of the medical instrument 7 when the connector portion 16 is connected to the attachment portion 6.

The drive mechanism 25 includes ball screws 26 that are linearly moved parallel to the sixth axis A so as to push and pull the motive power transmission members 11, motors 29 that rotate nuts 27 engaged with the ball screws 26, and gears 28 that transmit rotation of the motors 29 to the nuts 27. The motors 29 of the drive mechanism 25 are also provided with encoders (not illustrated) that detect the rotation angles of the motors 29.

The attachment portions 6 provided at the distal ends of the two robots 3A, 3B respectively have a common shape so that the same medical instrument 7 can be detachably attached thereto.

The switching devices 8A, 8B are, for example, state switching switches that can switch between a first state and a second state. The switching device 8A is connected between the main input device 4 and the processor 9, and the switching devices 8B are, for example, foot switches and are connected between the processor 9 and the robots 3A, 3B. For example, when the main input device 4 is switched to the first state in which the operation input from the main input device 4 is enabled, the operation input from the sub input devices 5 becomes disabled, and when the sub input devices 5 are switched to the second state in which the operation input from the sub input devices 5 is enabled, the operation input from the main input device 4 becomes disabled.

In addition, the medical system 1 may be provided with a mode switching switch (switch) 19D that enables selection of a synchronous mode in which the motor is driven to rotate the medical instrument driving portion 24 synchronously about the sixth axis A when the grip 18 is rotated about the sixth axis A, and an asynchronous mode in which the medical instrument driving portion 24 is not rotated.

Figure 4:
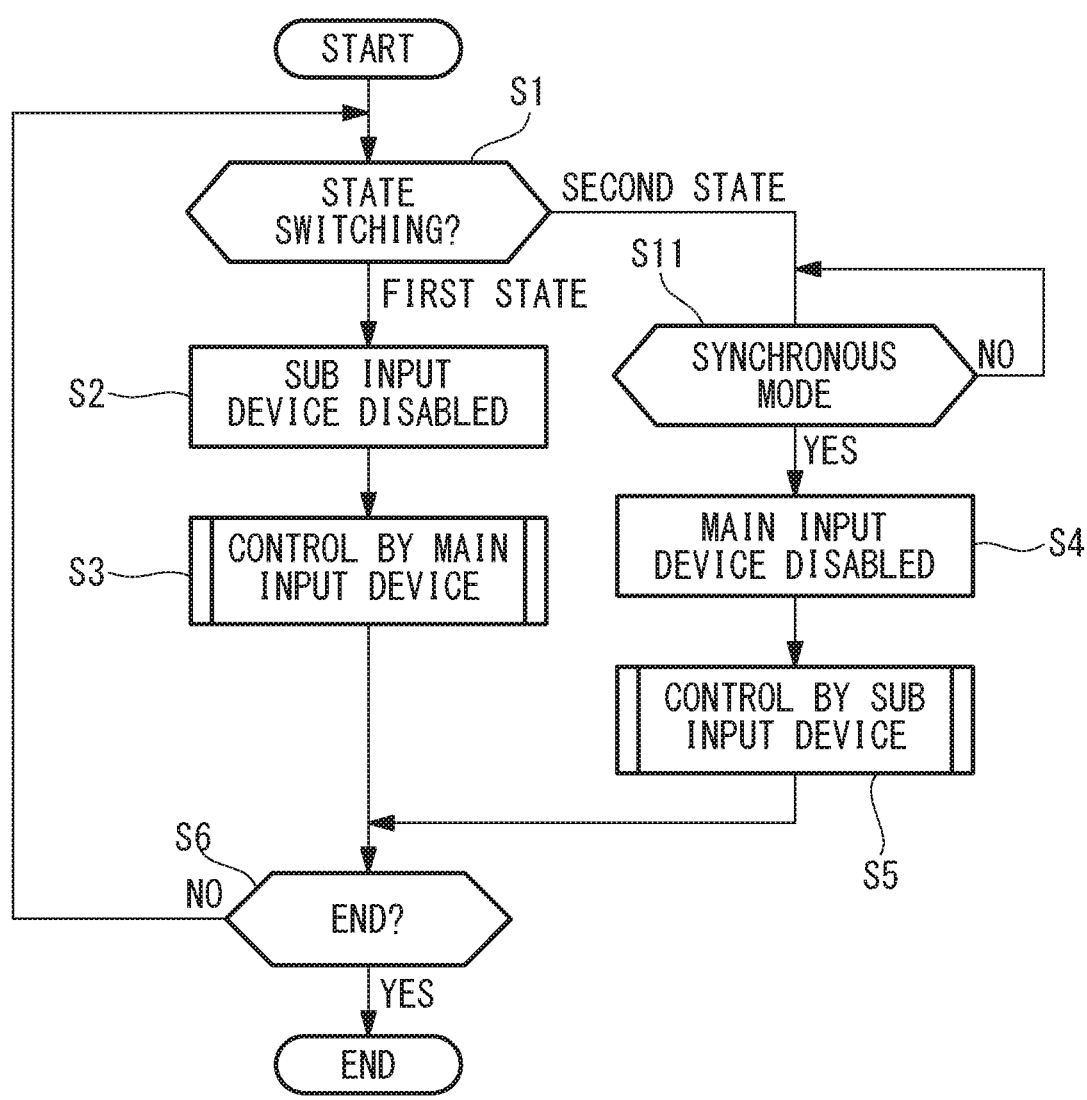
FIG. 4 is a flowchart illustrating control of the medical system in FIG. 1.

As illustrated in FIG. 4, upon operation of the switching devices 8A, 8B provided in the main input device 4 and the sub input devices 5, the processor 9 determines whether the operation has been switched to the first state or the second state (step S1), and when switched to the first state, the operation input from the sub input devices 5 is disabled (step S2), and the robots 3A, 3B and the medical instrument 7 are controlled by the operation input from the main input device 4 (step S3).

Figure 5:
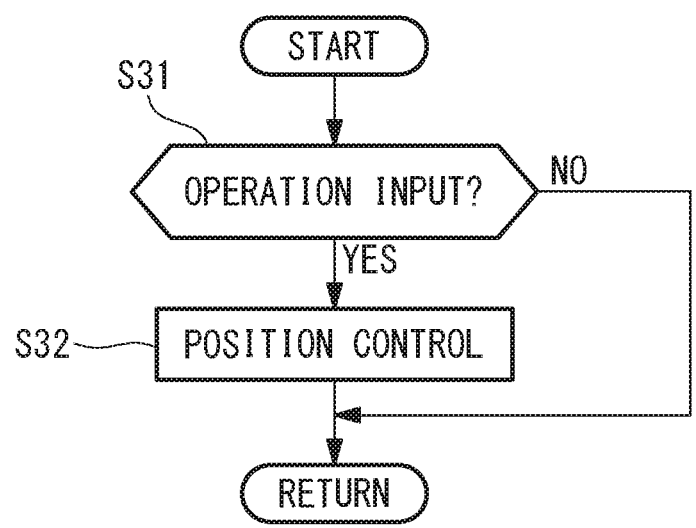
FIG. 5 is a flowchart illustrating control by a main input device in control of the medical system in FIG. 4.

That is, in step S3, as illustrated in FIG. 5, the processor 9 determines whether there is an operation input from the main input device 4 (step S31), and if an operation input is present, depending on the operation input that is input, the processor 9 supplies a drive command signal for driving the motors of the joints 10A, 10B, 10C, 10D, 10E, 10F of the robots 3A, 3B and the motors 29 of the medical instrument driving portion 24 provided at the distal end of the wrist (specifically, a drive command signal is transmitted to a driver (not illustrated) that drives the motors 29). Then, the positions of the robots 3A, 3B and the medical instruments 7 are controlled by adjusting the drive command signal (step S32) so that the deviation between the angle signal detected by each of the joints 10A, 10B, 10C, 10D, 10E and the encoders of the drive mechanisms 25 and the operation input becomes zero. In addition, if there is no operation input in step S31, a step S6 described later is executed.

On the other hand, as illustrated in FIG. 4, when the processor 9 is switched to the second state by the operation of the switching devices 8A, 8B in step S1, it is determined whether the mode is the synchronous mode or the asynchronous mode (step S11) and the process is repeated until the synchronous mode is selected, and when it is determined that the mode is the synchronous mode, the operation input from the main input device 4 is disabled (step S4), and the robots 3A, 3B and the medical instrument 7 are controlled by the operation input from the sub input devices 5 (step S5).

Figure 6:
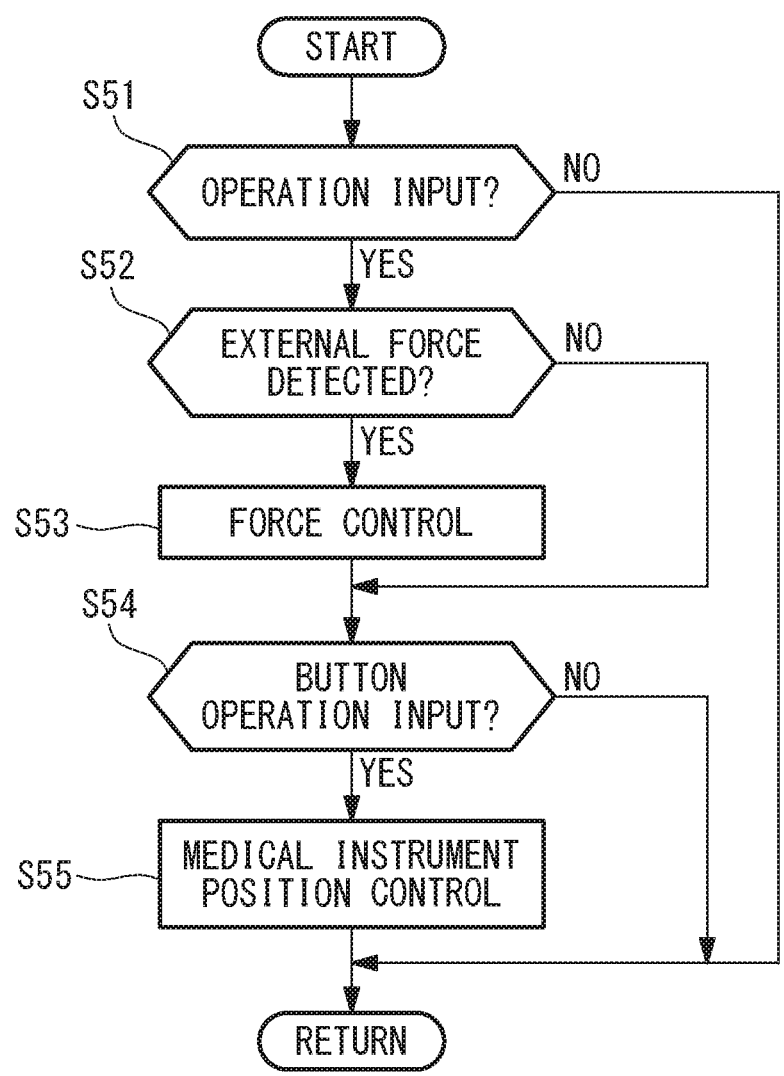
FIG. 6 is a flowchart illustrating control by a sub input device in control of the medical system in FIG. 4.

That is, in step S5, the processor 9 determines whether or not there is an operation input from the sub input devices 5, as illustrated in FIG. 6 (step S51), and when an operation input exists, it is determined whether or not the force sensors provided at the joints 10A, 10B, 10C, 10D, 10E of the robots 3A, 3B have detected an external force due to the surgeon who is holding the grips 18 applying an external force to the grips 18 (step S52), and, if an external force is detected, based on the operation input corresponding to the detected external force, a drive command signal is supplied to the motor of each of the joints 10A, 10B, 10C, 10D, 10E so that each of the joints 10A, 10B, 10C, 10D, 10E rotates in the direction of the external force. The robots 3A, 3B are force-controlled by adjusting the drive command signals so that the magnitude of the external force detected by the force sensors of the joints 10A, 10B, 10C, 10D, 10E becomes zero (step S53).

In addition, in the case where no external force is detected in step S52 and after executing step S53, the processor 9 determines whether or not the mode switching switch 19D provided on the grip 18 of the sub input device 5 has been operated (step S54), and, when an operation input for operating the manipulator portion 14 and the treatment portion 15 of the medical instrument 7 is input, a drive command signal for driving the motors 29 of the medical instrument drive portion 24 provided at the distal end of the wrist is supplied (specifically, a drive command signal is transmitted to drivers for driving the motors 29), and the positions of the manipulator portion 14 and the treatment portion 15 are controlled (step S55). After the position control of the manipulator portion 14 and the treatment portion 15, or in the case where the mode switching switch 19D is not operated in step S54, it is determined whether or not to end the operation (step S6), and in the case where it is determined to not end the operation, the process from step S1 is repeated.

In addition, when the processor 9 is switched to the synchronous mode by pressing of the mode switching switch 19D provided on the grip 18 of the sub-input device 5 (mode switching input is performed), the motor of the joint 10F is driven according to the rotation of the grip 18. Specifically, a signal regarding rotation information of the grip 18 is sent to the processor 9. Then, the processor 9 determines whether the input is for the synchronous mode or the asynchronous mode. In the case where it is determined that the synchronous mode has been input, the rotation amount of the joint 10F is calculated, and a signal related to the calculated rotation amount is transmitted to a driver that drives a motor corresponding to the joint 10F. Further, in the synchronous mode, the rotation amount is calculated so as to be substantially the same as the rotation amount of the grip 18, and a signal based on the calculation result is transmitted from the processor 9 to the driver that drives the motor corresponding to the joint 10F. Consequently, the medical instrument 7 can also be rotated according to the rotation of the grip 18.

Conversely, when the processor 9 is switched to the asynchronous mode by releasing the pressing of the mode switching switch 19D provided on the grip 18 of the sub input device 5 (mode switching input is performed), the motor of the joint 10F is not driven according to the rotation of the grip 18. Specifically, similarly to the synchronous mode, a signal regarding rotation information of the grip 18 is sent to the processor 9. Then, the processor 9 determines whether the input is for the synchronous mode or the asynchronous mode. In the case where it is determined that the asynchronous mode has been input, without calculating the rotation amount (movement amount) of the joint 10F, and regardless of the rotation amount of the grip 18, a signal is transmitted from the processor 9 to the driver that drives the motor corresponding to the joint 10F so that the rotation amount (movement amount) of the joint 10F becomes zero. That is, even if the grip 18 is rotated, the medical instrument 7 does not rotate (does not operate).

In addition, for example, in the asynchronous mode, the surgeon can hold the grip 18 and switch to the synchronous mode when the direction in which the surgeon can easily operate has been determined. Consequently, the medical instrument 7 can be rotated after adjusting the direction of the grip 18 in a direction easy for the surgeon to operate without rotating the medical instrument 7 about the longitudinal axis.

The operation of the medical system 1 according to the present embodiment configured as described above will be described below.

When performing an operation on a patient using the medical system 1 according to the present embodiment, the insertion portions 13 of the two medical instruments 7 attached to the distal ends of the two robots 3A and 3B are inserted into the body via through-holes formed through the body tissue of the patient lying on the bed 2, and the treatment portions 15 at the distal ends of the insertion portions 13 are arranged under observation by an endoscope (not illustrated).

In this state, by using the switching device 8A of the main input device 4, the surgeon switches the main input device 4 to the first state in which the operation input from the main input device 4 is enabled and operates the left and right handles 17 so that an operation input performed by the handles 17 is supplied to the processor 9. Thereby, the processor 9 drives the motors of the joints 10A, 10B, 10C, 10D, 10E of the two robots 3A, 3B, and the treatment portions 15 are arranged at desired positions and orientations. In addition, when the surgeon operates the handles 17 of the main input device 4, the manipulator portion 14 and the treatment portion 15 of the medical instruments 7 are operated, and the affected part of the patient's body can be treated.

On the other hand, if the surgeon needs to perform an operation in a situation where he is away from the main input device 4 and is beside the patient and examining the patient, the surgeon switches to the second state in which the operation input from the sub input devices 5 is enabled by using the switching devices 8B provided on the grips 18 of the sub input devices 5 attached to the distal ends of the corresponding robots 3A, 3B. Then, when the surgeon holds the grips 18 and applies an external force, the joints 10A, 10B, 10C, 10D, 10E of the robots 3A, 3B are operated in accordance with the applied external force, and the distal ends of the robots 3A, 3B can be moved to desired positions. In addition, by pressing the buttons 19A, 19B, 19C provided on the grips 18, the manipulator portions 14 and the treatment portions 15 of the medical instruments 7 can be operated to treat the affected part of the patient's body.

As described above, in the medical system 1 according to the present embodiment, not only is the main input device 4 disposed remote from the patient but also the sub input devices 5 that the surgeon holds and to which the surgeon directly applies a force are provided at the distal ends of the robots 3A, 3B; consequently, there is an advantage that the surgeon can continue treatment even when changing the installation position of the robots 3A, 3B due to a change of the operative field (change of treatment target site) or the like during the operation.

In addition, in the medical system 1 according to the present embodiment, the case where the medical instruments 7 are attached to the corresponding two robots 3A, 3B has been exemplified; however, instead of this, the medical instrument 7 may be attached to only one robot 3A, and the operation may be performed without using the other robot 3B. In this case, when the position (operative field) of the affected part to be treated is markedly changed while the treatment is being performed by the one robot 3A, a situation may occur in which the treatment portion 15 at the distal end of the medical instrument 7 cannot be moved to a desired position due to the operating limit of the one robot 3A.

In such a case, since the operating ranges of the two robots 3A, 3B are usually different, the connector portion 16 of the medical instrument 7 may be separated from the attachment portion 6 of the one robot 3A, and the connector portion 16 of the medical instrument 7 may be re-attached to the attachment portion 6 of the other robot 3B. By doing so, after re-attachment, the treatment portion 15 at the distal end of the medical instrument 7 can be moved in accordance with the operating range of the other robot 3B, and an operative field that has been markedly changed can be treated. Then, in this case, there is an advantage in that it is possible to carry out the re-attachment without removing the insertion portion 13 of the medical instrument 7 from the through hole formed through the body surface tissue of the patient, thereby shortening the operation time and reducing the burden on the patient.

Further, in the medical system 1 according to the present embodiment, the case where two robots 3A, 3B are provided is illustrated; however, the present invention may be applied to a case where one or more arbitrary number of robots 3A, 3B are provided instead.

In addition, the axis configuration of the robots 3A, 3B and the type of the medical instrument 7 may be arbitrary.

In addition, in the present embodiment, in the operation of rotating the medical instrument 7 by the rotation of the grip 18, the operation is switched between the synchronous mode and the asynchronous mode by using the mode switching switch 19D; however, alternatively, the switching may be performed in accordance with the presence or absence of an operation command signal for driving the motor, output from the processor 9.

In addition, the switching devices 8A, 8B are provided for the main input device 4 and the sub input devices 5, respectively; however, so long as another configuration has the function of the switching devices 8A, 8B, a device having only one of the switching devices 8A, 8B may be employed, or a device having neither of the switching devices 8A, 8B may be employed.

In addition, alternatively, in the case where an operation input by the sub input devices 5 is performed while the main input device 4 is not being operated, control may be switched to control by the sub input devices 5, and when an operation input by the main input device 4 is performed without operating the sub input devices 5, control may be switched to control by the main input device 4.

In addition, the mode switching switch 19D may have the function of the switching devices 8A, 8B. In this case, when the mode switching switch 19D is pressed, the mode is switched from the asynchronous mode to the synchronous mode, and is also switched from the first state to the second state.

In addition, when one of the main input device 4 and the sub input devices 5 is operated and an operation input is performed by the other, an alarm may be issued.

Figure 7:
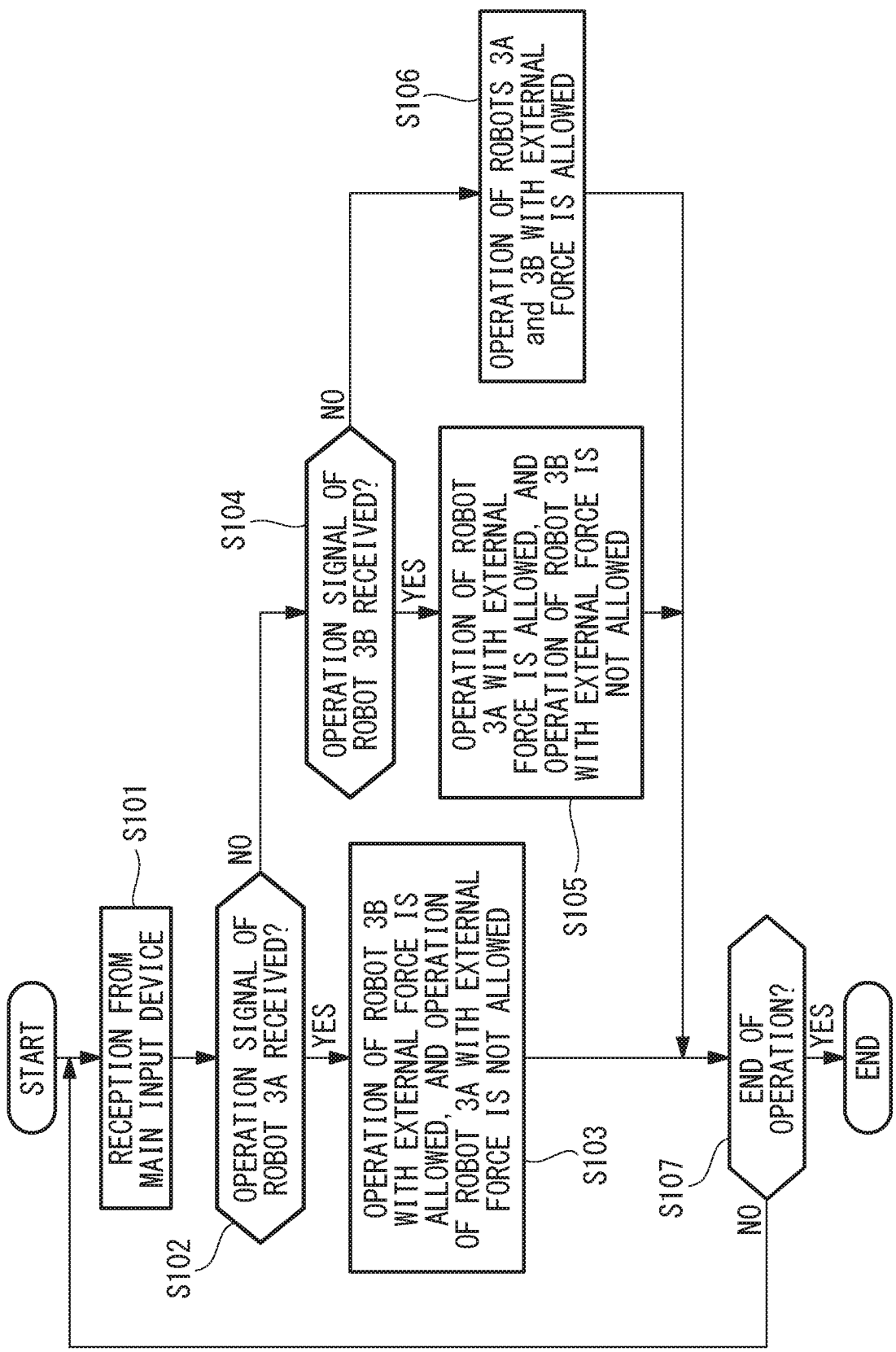
FIG. 7 is a flowchart illustrating a modification of the control of the medical system in FIG. 4.

In addition, in the medical system 1 according to the present embodiment, as illustrated in FIG. 7, the control of the operation of each of the robots 3A, 3B may be switched on the basis of a signal received from the main input device 4. Specifically, a reception signal is received from the main input device 4 (step S101), and the processor 9 determines whether a signal for operating the robot 3A among the two robots 3A, 3B is received (step S102). When it is determined that a signal for operating the robot 3A has been received, in the robot 3B, operation of each of the joints 10A, 10B, 100, 10D, 10E of the robot 3B with an external force applied to the grip 18 or the like is allowed, and operation of the robot 3A with an external force is not allowed (step S103).

In addition, if it is determined in step S102 that a signal for operating the robot 3A has not been received, it is determined whether a signal for operating the robot 3B has been received (step S104). Then, when it is determined that a signal for operating the robot 3B has been received, that is, when the processor 9 does not receive a signal for operating the robot 3A from the main input device 4 (the handle 17) and receives a signal for operating the robot 3B from the main input device 4 (the handle 17), in the robot 3A, operation of the joints 10A, 10B, 100, 10D, 10E of the robot 3A with an external force applied to the grip 18 or the like is allowed (step S105). In this case, in the robot 3B, even if an external force is applied to the grip 18 or the like, the joints 10A, 10B, 100, 10D, 10E of the robot 3B are not allowed to operate in accordance with the external force.

In addition, if it is determined in step S104 that a signal for operating the robot 3B has not been received, in the two robots 3A, 3B, operation of the joints 10A, 10B, 100, 10D, 10E of the robots 3A, 3B with an external force applied to the grip 18 or the like is allowed (step S106). After execution of steps S103, S105, and S106, it is determined whether or not to end the operation (step S107), and, if it is determined that the operation is to be continued, the process from step S102 is executed.

Figure 8:
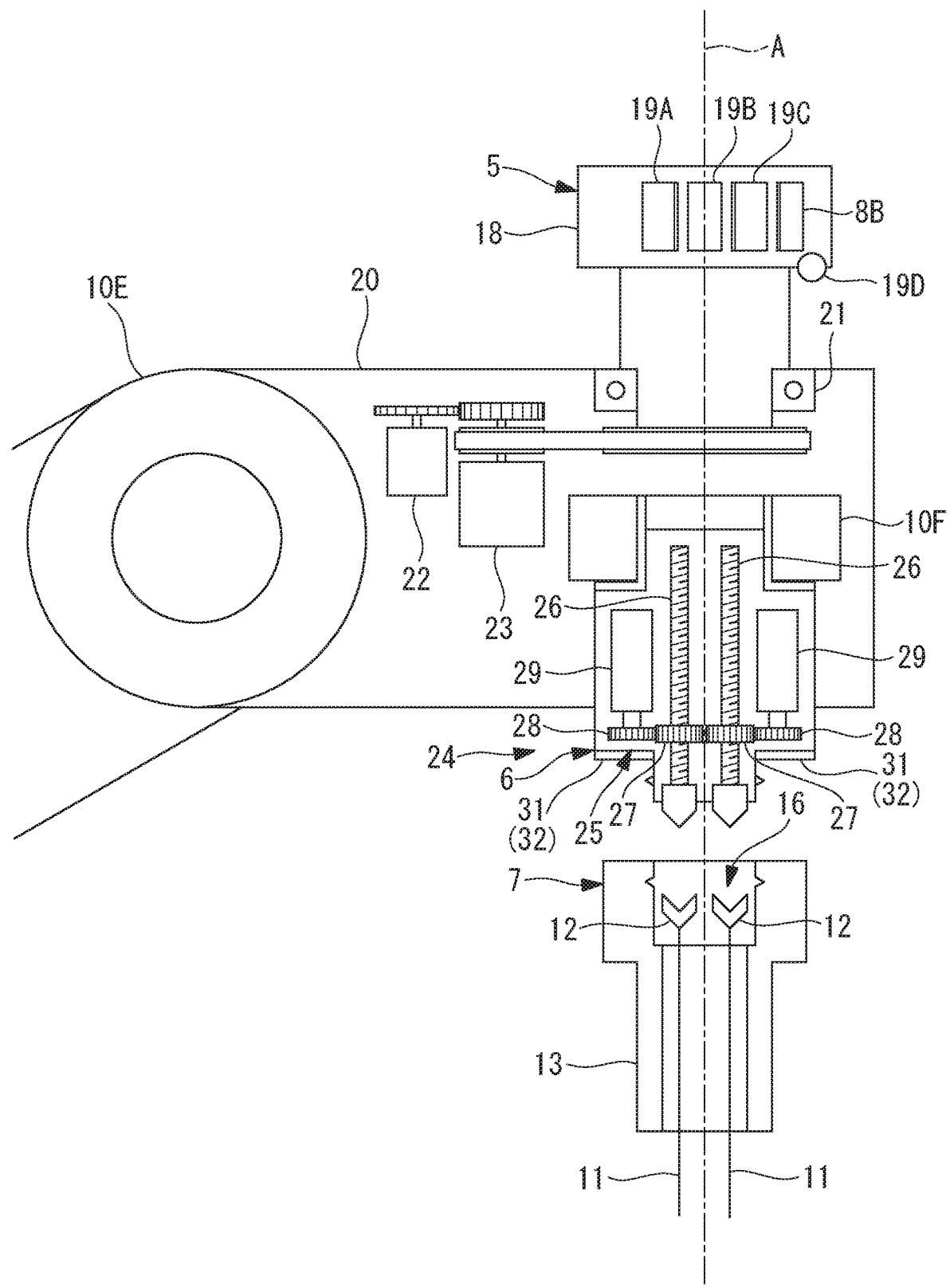
FIG. 8 is a diagram illustrating a modification of the medical system in FIG. 1.

In addition, in the medical system 1 according to the present embodiment, the attachment and detachment of the medical instruments 7 to and from the two robots 3A, 3B may be detected. Specifically, as illustrated in FIG. 8, the robot 3A includes a first detector 31 that detects attachment and detachment of the medical instrument 7 to and from the attachment portion 6, and the robot 3B includes a second detector 32 that detects attachment and detachment of the instrument 7 to and from the attachment portion 6. The first detector 31 and the second detector 32 are, for example, contact sensors or pressure sensors.

In addition, the processor 9 may receive a signal based on the detection result detected by the first detector 31 and the second detector 32 and operate the medical instrument 7 on the basis of the signal.

Consequently, as illustrated in FIG. 9, when the medical instrument 7 attached to the robot 3A is removed (step S201), the removal of the medical instrument 7 is detected by the first detector 31, and, on the basis of the detection result, the processor 9 allows the joints 10A, 10B, 10C, 10D, 10E of the robot 3A to be operated with an external force (step S202), and disables the operation of the medical instrument 7 through input of the sub input device 5 of the robot 3A (step S203). Then, when the detached medical instrument 7 is mounted on the robot 3B (step S204), the attachment of the medical instrument 7 is detected by the second detector 32, and, on the basis of the detection result, the processor 9 allows the joints 10A, 10B, 10C, 10D, 10E of the robot 3B to be operated with an external force (step S205), and can enable the operation of the medical instrument 7 through input of the sub input device 5 of the robot 3B (Step S206).

The above-described embodiment also leads to the following aspects.

According to an aspect of the present invention, a medical system includes: a medical instrument that has a treatment portion at a distal end thereof; at least one arm that includes at least one joint and at least one driving device that drives the at least one joint, the at least one arm including an attachment portion for detachably attaching the medical instrument at a distal end; a first input device located remote from the at least one arm, the first input device being configured to perform an operation input for operating the medical instrument and the at least one arm, the medical instrument being attached to the attachment portion of the at least one arm; a second input device provided at a distal end of the at least one arm, the second input device being configured to perform an operation input for operating the medical instrument and the at least one arm, the medical instrument being attached to the attachment portion of the at least one arm; and a processor that controls the at least one arm and the medical instrument on the basis of an operation input that is input from the first input device or the second input device. The medical system enables switching in order to selectively accept an operation input from the first input device or the second input device.

According to this aspect, in the case where a surgeon can operate the first input device that is located remote from the arm, when the first input device is operated by switching so that only an operation input from the first input device is accepted, based on the operation input that is input from the first input device, the processor can control the arm and the medical instrument attached to the attachment portion at the distal end of the arm to perform treatment on the patient. On the other hand, in a situation where the surgeon is beside the patient, when the second input device is operated by switching so that only an operation input from the second input device is accepted, based on the operation input that is input from the second input device, the processor can control the arm and the medical instrument to perform treatment on the patient.

That is, according to this aspect, in a medical system for operating on a patient through a first input device that is remote from the patient, even when changing the installation position of an arm due to a change of the operative field (change of treatment target site) or the like during the operation, the surgeon can continue the treatment.

In the above aspect, the medical system may further include a switching device that enables switching in order to selectively accept an operation input from the first input device or the second input device.

In addition, in the above aspect, the at least one joint of the at least one arm may include a sensor configured to detect an external force, the second input device may enable input of an external force applied to the distal end of the at least one arm as the operation input, and when the switching device has been operated so that the operation input from the second input device is accepted, the processor may control the driving device of the at least one joint on the basis of the external force detected by the sensor.

By doing this, when the switching device is operated so that only an operation input from the second input device is accepted, if an external force is applied to the second input device, the external force applied to the distal end of the arm is detected by a sensor provided at each joint of the arm, and the driving device of the joint is controlled by the processor on the basis of the detected external force. Consequently, the medical instrument is controlled by the second input device while operating the arm in an orientation according to an external force applied to the distal end of the arm, so that the operation on the patient can be performed more intuitively.

In addition, in the above aspect, the at least one arm may include at least a first arm and a second arm, and, when the processor does not receive a signal for operating the first arm from the first input device and receives a signal for operating the second arm from the first input device, in the first arm, operation of the at least one joint of the first arm may be allowed when an external force acts on the first arm, and in the second arm, operation of the at least one joint of the second arm may not be allowed when an external force acts on the second arm.

In addition, in the above aspect, the at least one arm may include at least two arms, and the attachment portion of each of the at least two arms may be configured to enable attachment of the same medical instrument.

By doing this, in a state in which an operation is being performed with a medical instrument attached to the attachment portion of one arm, in the case where the operative field is to be changed outside the operating range of the one arm in order to continue the operation, by removing the medical instrument from the attachment portion of the one arm and attaching the medical instrument to the attachment portion of another arm, surgery can be performed within the operating range of the other arm. Consequently, for example, by simply changing the attached arm while maintaining the state in which the treatment portion of the medical instrument is inserted into the body, the range in which treatment can be performed by the treatment portion can be changed, and the burden on the patient can be reduced.

In addition, in the above aspect, the second input device may include a grip rotatable about a longitudinal axis of the medical instrument attached to the attachment portion, and a switch, and the processor, on the basis of a signal from the switch, may switch between a synchronous mode in which the medical instrument is rotated about the longitudinal axis in synchronization with rotation of the grip, and an asynchronous mode in which the medical instrument is not rotated even when the grip is rotated.

Thus, when the switch is operated to switch to the synchronous mode, the medical instrument is rotated about the longitudinal axis in synchronization with the rotation of the grip of the second input device. On the other hand, when the switch is operated to switch to the asynchronous mode, the medical instrument does not rotate around the longitudinal axis regardless of the rotation of the grip. In addition, for example, in the asynchronous mode, the surgeon holds the grip and when a direction in which it is easy for the surgeon to operate is determined, the surgeon can switch to the synchronous mode. Consequently, the medical instrument can be rotated after adjusting the direction of the grip to be a direction in which it is easy for the surgeon to operate without rotating the medical instrument about the longitudinal axis.

In addition, in the above aspect, the second input device may include a grip rotatable about a longitudinal axis of the medical instrument attached to the attachment portion, and a switch provided on the grip, and the processor, on the basis of a signal from the switch, may switch between a synchronous mode in which the medical instrument is rotated about the longitudinal axis in synchronization with rotation of the grip, and an asynchronous mode in which the medical instrument is not rotated even when the grip is rotated, and may switch between a first state in which the operation input of the first input device is enabled and the operation input of the second input device is disabled, and a second state in which the operation input of the second input device is enabled and the operation input of the first input device is disabled.

In addition, in the above aspect, the at least one arm may include at least a first arm and a second arm, the attachment portion of the first arm may have a first detector that detects attachment and detachment of the medical instrument, the attachment portion of the second arm may have a second detector that detects attachment and detachment of the medical instrument, and the processor, when the medical instrument attached to the first arm is to be removed, on the basis of a detection result detected by the first detector, may disable operation of the medical instrument through input of the second input device of the first arm while allowing operation of the at least one joint of the first arm with an external force acting on the first arm, and when the medical instrument is mounted on the second arm, may enable operation of the medical instrument through input of the second input device of the second arm while allowing operation of the at least one joint of the second arm with an external force acting on the second arm.

REFERENCE SIGNS LIST 1 medical system
3A, 3B robot (arm)
4 main input device (first input device)
5 sub input device (second input device)
6 attachment portion
7 medical instrument
8A, 8B switching device
9 processor
10A, 10B, 100, 10D, 10E joint
15 treatment portion
18 grip
19D mode switching switch (switch)
31 first detector
32 second detector

The invention claimed is:

1. A medical system comprising:
a medical instrument that has a treatment portion at a distal end thereof;
at least one arm that includes at least one joint and at least one motor that drives the at least one joint, the at least one arm including an attachment portion for detachably attaching the medical instrument at a distal end;
a first input device that comprises a handle and that is located remote from the at least one arm, the first input device being configured to perform an operation input for operating the medical instrument and the at least one arm, the medical instrument being attached to the attachment portion of the at least one arm;
a second input device provided at a distal end of the at least one arm, the second input device being configured to perform an operation input for operating the medical instrument and the at least one arm, the medical instrument being attached to the attachment portion of the at least one arm; and
a processor that controls the at least one arm and the medical instrument on the basis of an operation input that is input from the first input device or the second input device,
wherein the medical system enables switching in order to selectively accept an operation input from the first input device or the second input device,
the second input device comprises a grip rotatable about a longitudinal axis of the medical instrument attached to the attachment portion, and a first switch, and
the processor, on the basis of a signal from the first switch, switches between a synchronous mode in which the medical instrument is rotated about the longitudinal axis in synchronization with rotation of the grip, and an asynchronous mode in which the medical instrument is not rotated even when the grip is rotated.

2. The medical system according to claim 1, further comprising:
a second switch that enables switching in order to selectively accept an operation input from the first input device or the second input device.

3. The medical system according to claim 2, wherein the at least one joint of the at least one arm includes a sensor configured to detect an external force,
the second input device enables input of an external force applied to the distal end of the at least one arm as the operation input, and
when the second switch has been operated so that the operation input from the second input device is accepted, the processor controls the at least one motor of the at least one joint on the basis of the external force detected by the sensor.

4. The medical system according to claim 1, wherein the at least one arm comprises at least a first arm and a second arm, and
when the processor does not receive a signal for operating the first arm from the first input device and receives a signal for operating the second arm from the first input device, in the first arm, operation of the at least one joint of the first arm is allowed when an external force acts on the first arm, and in the second arm, operation of the at least one joint of the second arm is not allowed when an external force acts on the second arm.

5. The medical system according to claim 1, wherein the at least one arm comprises at least two arms, and
the attachment portion of each of the at least two arms is configured to enable attachment of the same medical instrument.

6. The medical system according to claim 1, wherein the first switch is provided on the grip, and
the processor, on the basis of a signal from the first switch, switches between a first state in which the operation input of the first input device is enabled and the operation input of the second input device is disabled, and a second state in which the operation input of the second input device is enabled and the operation input of the first input device is disabled.

7. The medical system according to claim 1, wherein the at least one arm comprises at least a first arm and a second arm,
the attachment portion of the first arm has a first detector that detects attachment and detachment of the medical instrument,
the attachment portion of the second arm has a second detector that detects attachment and detachment of the medical instrument, and
the processor, when the medical instrument attached to the first arm is to be removed, on the basis of a detection result detected by the first detector, disables operation of the medical instrument through input of the second input device of the first arm while allowing operation of the at least one joint of the first arm with an external force acting on the first arm, and when the medical instrument is mounted on the second arm, enables operation of the medical instrument through input of the second input device of the second arm while allowing operation of the at least one joint of the second arm with an external force acting on the second arm.

8. A medical system comprising:
an arm that is configured to attach a medical instrument having a treatment portion at a distal end thereof and that includes at least one joint, the arm comprising:
a sensor provided at the at least one joint, the sensor detecting an external force applied to the arm;
a first motor that drives the at least one joint; and
a second motor that drives the medical instrument;
a first input device that comprises a handle and that is located remote from the arm, the first input device being configured to perform an operation input for operating the medical instrument and the arm;
a second input device provided at a distal end of the arm, the second input device being configured to perform an operation input for operating the medical instrument and the arm, the second input device comprising:
a grip provided at an end of the arm to directly operate the arm;
a button provided at the grip to operate the medical instrument; and
a switch that enables switching in order to selectively accept an operation input from the first input device or the second input device; and
a processor that controls the first motor and the second motor,
wherein the processor:
controls the first motor on the basis of an amount of the external force detected by the sensor when the grip is directly operated in a state where the operation input from the second input device is ready to be accepted;
detect, after controlling the first input device, whether or not the button is operated; and
control, in response to detecting that the button is operated, the second motor on the basis of the operation input of the second input device.

9. The medical system according to claim 8, wherein the processor drives the first motor or the second motor until the sensor detect no external force.

10. The medical system according to claim 8, wherein the at least one joint comprises a plurality of joints, and each of the plurality of joints includes the sensor and the first motor.

11. The medical system according to claim 8, wherein the grip is rotatable with respect to the arm, and
the processor, on the basis of a signal from the second input device, switches between a synchronous mode in which the medical instrument is rotated about a longitudinal axis of the medical instrument in synchronization with rotation of the grip, and an asynchronous mode in which the medical instrument is not rotated even when the grip is rotated.

* * * * *